(12) United States Patent
Kaneko

(10) Patent No.: US 7,886,574 B2
(45) Date of Patent: Feb. 15, 2011

(54) COLLISION TEST APPARATUS AND COLLISION TEST METHOD

(75) Inventor: Akira Kaneko, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 12/247,396

(22) Filed: Oct. 8, 2008

(65) Prior Publication Data
US 2009/0113987 A1 May 7, 2009

(30) Foreign Application Priority Data
Oct. 9, 2007 (JP) .............................. 2007-262939

(51) Int. Cl.
G01N 3/307 (2006.01)
G01M 7/04 (2006.01)
(52) U.S. Cl. ..................... 73/12.05; 73/12.01; 73/12.04
(58) Field of Classification Search ..... 73/12.01–12.05; 124/16–29
See application file for complete search history.

(56) References Cited

U.S. PATENT DOCUMENTS

| | | | | |
|---|---|---|---|---|
| 300,415 | A * | 6/1884 | Van Allen ................... | 124/20.1 |
| 1,034,716 | A * | 8/1912 | Kruger ........................ | 473/511 |
| 2,307,125 | A * | 1/1943 | Goddard ..................... | 244/63 |
| 3,572,311 | A * | 3/1971 | Baer ........................... | 124/20.1 |
| 3,879,982 | A * | 4/1975 | Schmidt ..................... | 73/12.01 |
| 3,949,729 | A * | 4/1976 | Pfotenhauer ............... | 124/20.3 |
| 4,034,603 | A * | 7/1977 | Leeb et al. ................. | 73/79 |
| 4,240,396 | A * | 12/1980 | Randoll ...................... | 124/17 |
| 4,313,337 | A * | 2/1982 | Myint ......................... | 73/12.13 |
| 4,435,976 | A * | 3/1984 | Edward, Jr. ................ | 73/83 |
| 4,909,518 | A * | 3/1990 | Erlandson et al. ........... | 273/357 |
| 5,036,696 | A * | 8/1991 | Ahrens et al. .............. | 73/12.11 |

(Continued)

FOREIGN PATENT DOCUMENTS

JP 58-195798 A 11/1983

(Continued)

OTHER PUBLICATIONS

"Substantially" Merriam-Webster, Inc. Webster's Ninth New Collegiate Dictionary. Springfield, Mass: Merriam-Webster, 1983.*

(Continued)

*Primary Examiner*—Lisa M Caputo
*Assistant Examiner*—Jonathan Dunlap
(74) *Attorney, Agent, or Firm*—Birch, Stewart, Kolasch & Birch, LLP

(57) ABSTRACT

A projection device is configured by connecting a projectile supporting part to a spring supporting frame with multiple coil springs. The projectile supporting part is pulled while deforming the coil springs; a projectile is projected by accelerating the projectile supporting part, supporting the projectile, with restoring forces of the coil springs; and the projectile is collided with a test piece supported by the test piece supporting base. Thereby, it is possible to check a state of collision of the projectile with the test piece or how the test piece is damaged thereby. Since the projectile is projected with the restoring forces of the deformed coil springs, the collision test apparatus is simple and compact in structure, low-cost, and easy-to-handle in comparison with projection of a projectile with compressed air.

16 Claims, 11 Drawing Sheets

U.S. PATENT DOCUMENTS

| | | | |
|---|---|---|---|
| 5,141,236 A * | 8/1992 | Petitto | 473/511 |
| 5,184,499 A * | 2/1993 | Oppliger et al. | 73/11.01 |
| 5,303,695 A * | 4/1994 | Shopsowitz | 124/17 |
| 5,551,412 A * | 9/1996 | Warnke | 124/20.1 |
| 5,694,913 A * | 12/1997 | Parrott | 124/17 |
| 6,210,285 B1 * | 4/2001 | Susko | 472/50 |
| 6,769,287 B2 * | 8/2004 | Stewart et al. | 73/12.01 |
| 7,461,645 B2 * | 12/2008 | Williamson et al. | 124/20.1 |
| 2004/0112353 A1 * | 6/2004 | Stewart et al. | 124/20.1 |

FOREIGN PATENT DOCUMENTS

| | | | |
|---|---|---|---|
| JP | 61-247941 A | 11/1986 | |
| JP | 2005-55216 A | 3/2005 | |

OTHER PUBLICATIONS

"Perpendicular." Merriam-Webster Online Dictionary. 2010. Merriam-Webster Online. Jan. 4, 2010 <http://www.merriam-webster.com/dictionary/perpendicular>.*

"Parallel." Merriam-Webster Online Dictionary. 2010. Merriam-Webster Online. Jan. 4, 2010 <http://www.merriam-webster.com/dictionary/parallel>.*

* cited by examiner

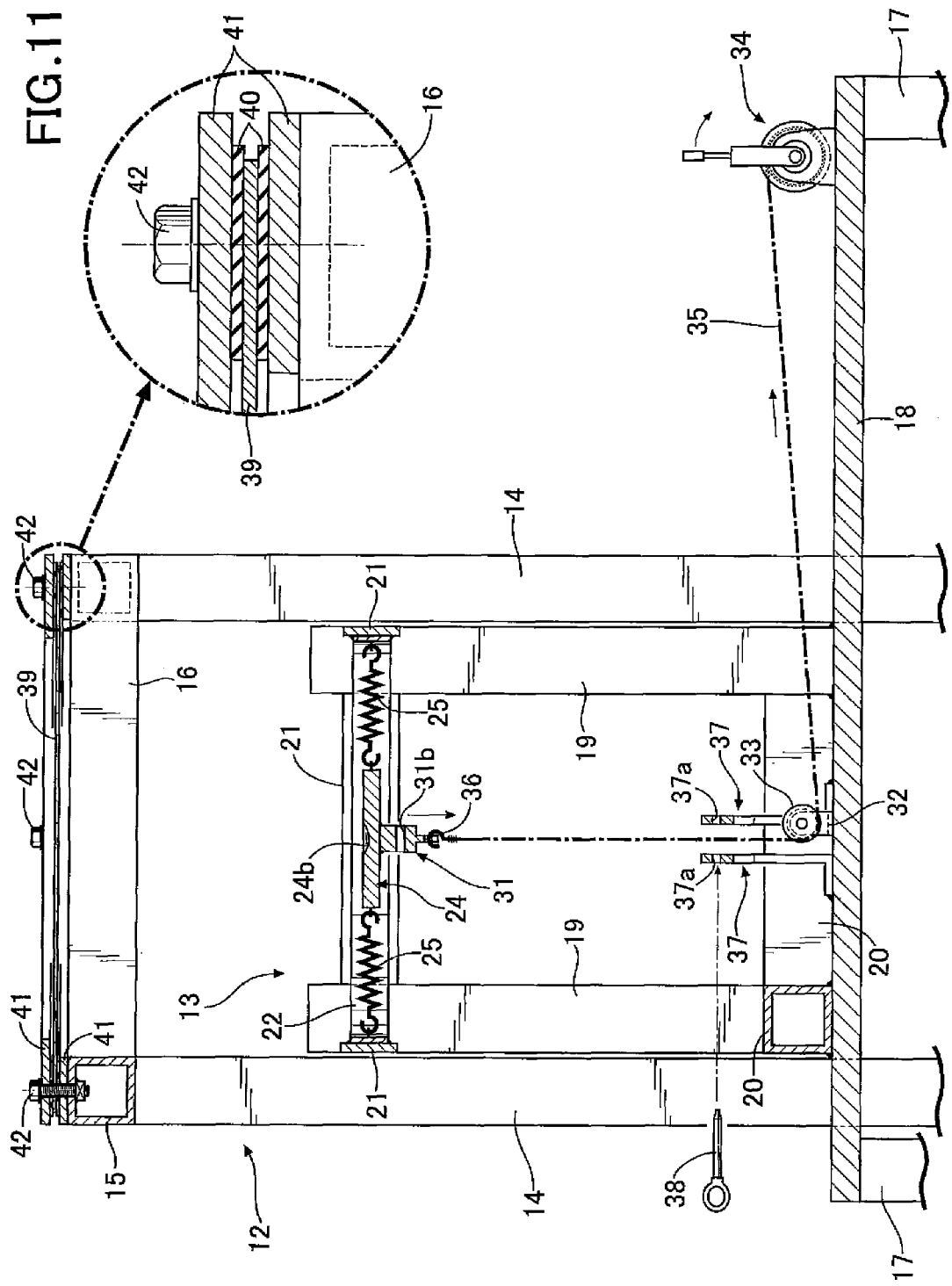

COLLISION TEST APPARATUS AND COLLISION TEST METHOD

BACKGROUND OF THE INVENTION

1. Field of the Invention

The present invention relates to a collision test apparatus and a collision test method which collide a projectile projected from a projection device with a test piece supported by a test piece supporting base for checking a state of collision of the projectile with the test piece or how the test piece is damaged thereby.

2. Description of the Related Art

Japanese Patent Application Laid-open No. 58-195798 has made publicly known an object ejecting apparatus for conducting a strength test by colliding a bird with a windshield glass of an aircraft at a predetermined speed, or colliding an object such as a stone with a construction material at a predetermined speed. The object ejecting apparatus includes a sabot supporting an ejected object at the sabot's front end, the sabot housed movably in a cylinder, and makes the sabot collide with stoppers by accelerating the sabot by use of compressed air reserved in an air tank to thereby eject the object.

Furthermore, Japanese Patent Application Laid-open No. 61-247941 has made publicly known a shooting apparatus for conducting an impact resistance test by colliding a projectile, such as a steel ball, with a fuselage or windshield glass of an aircraft. The shooting apparatus includes a valve element made of a rotary cylinder containing a projectile, the valve element being provided in a base part of a barrel connected to an air tank. The shooting apparatus releases pressurized air from the air tank by rotating the valve element to thereby eject the projectile through the barrel.

Moreover, Japanese Patent Application Laid-open No. 2005-55216 has made publicly known a hail impact test apparatus and method for testing the durability of a solar cell shell or a solar cell module by colliding an ice ball, imitating a piece of hail, with the solar cell shell or the solar cell module. The hail impact test apparatus ejects an ice ball contained in a shooting cylinder by use of compressed air reserved in an air tank.

These conventional types of test apparatus have such a structure that an object is projected by use of compressed air reserved in a pressure vessel. For this reason, these conventional types of test apparatus need to include such a pressure vessel and a pressure source for accumulating pressure in the pressure vessel. This brings about not only a problem that it is difficult to handle the test apparatus, but also a problem that the facilities have to be large so that the costs are accordingly pushed up.

SUMMARY OF THE INVENTION

The present invention has been made with the foregoing situations taken into consideration. An object of the present invention is to provide a collision test apparatus and a collision test method which are capable of projecting a projectile to a test piece accurately although the structure of the collision test apparatus is simple and economical.

In order to achieve the object, according to a first feature of the present invention, there is provided a collision test apparatus which collides a projectile projected from a projection device with a test piece supported by a test piece supporting base for checking a state of collision of the projectile with the test piece or how the test piece is damaged thereby, wherein the projection device is configured by connecting a projectile supporting part to a frame by use of an elastic body, the projectile supporting part supporting the projectile is pulled while deforming the elastic body, and the projectile is projected from the projectile supporting part by use of a restoring force of the elastic body.

With the foregoing configuration, the projection device is configured by connecting the projectile supporting part to the frame by use of the elastic body. Thus, the projectile supporting part is pulled while deforming the elastic body; the projectile is projected from the projectile supporting part supporting the projectile by use of a restoring force of the elastic body; and the projectile is collided with the test piece supported by the test piece supporting base. Thereby, the foregoing configuration makes it possible to check a state of collision of the projectile with the test piece or how the test piece is damaged thereby. Because the projectile is projected by use of the restoring force of the elastic body thus deformed, the foregoing configuration makes the collision test apparatus simple and compact in structure, low costs, and easy-to-handle in comparison with a configuration in which a projectile is projected by use of compressed air.

According to a second feature of the present invention, in addition to the first feature, the projectile is projected from the projectile supporting part when the projectile supporting part starts to be decelerated after ceasing to be accelerated.

With the foregoing configuration, the projectile is projected from the projectile supporting part when the projectile supporting part starts to be decelerated after ceasing to be accelerated. For this reason, the foregoing configuration makes it possible to stabilize the movement trajectory of the projectile supporting part and the projection direction of the projectile in comparison with a configuration in which a projectile is projected by colliding a projectile supporting part with stoppers while the projectile supporting part is still in the process of being accelerated.

According to a third feature of the present invention, in addition to the first feature, there is provided the collision test apparatus further comprising: pulling means for pulling the projectile supporting part by use of a wire; and locking means for locking the projectile supporting part to a pulling position, wherein the projectile is projected by releasing the projectile supporting part from being locked by the locking means.

The foregoing configuration provides the collision test apparatus with the pulling means for pulling the projectile supporting part by use of the wire, and the locking means for locking the projectile supporting part to the pulling position. For this reason, the foregoing configuration not only makes it easy to pull the projectile supporting part, but also makes it easy to project the projectile at an arbitrary timing by releasing the projectile supporting part being locked by the locking means.

According to a fourth feature of the present invention, in addition to the first feature, there is provided the collision test apparatus further comprising a stopper for stopping the projectile supporting part by abutting on the projectile supporting part after the projectile is projected therefrom.

The foregoing configuration provides the collision test apparatus with the stopper for stopping the projectile supporting part by abutting on the projectile supporting part after the projectile is projected. For this reason, the foregoing configuration makes it possible to prevent the projectile supporting part from overpassing its initial position to a large extent, and thus from interfering with any other body. Moreover, because the stopper abuts on the projectile supporting part after the projectile is projected, the foregoing configuration prevents the projection direction of the projectile from deviating due to an impact generated by the abutment.

According to a fifth feature of the present invention, in addition to the first feature, there is provided the collision test apparatus further comprising: a guide rod which is slidably fitted into a guide hole formed in the projectile supporting part, and a guide cylinder for guiding the projectile projected from the projectile supporting part to the test piece.

The foregoing configuration provides the collision test apparatus with the guide rod which is slidably fitted into the guide hole formed in the projectile supporting part. For this reason, when the projectile is projected, the foregoing configuration makes it possible to stabilize the movement trajectory of the projectile supporting part, and to reduce the deviation of the projection direction of the projectile to a minimum. In addition, the foregoing configuration provides the collision test apparatus with the guide cylinder for guiding the projectile projected from the projectile supporting part to the test piece. For this reason, the foregoing configuration makes it possible to correctly collide the projectile with the test piece at its target collision position by correcting the collision direction of the projectile by use of the guide cylinder even if the projected direction of the projectile deviates to some extent.

According to a sixth feature of the present invention, in addition to the first feature, the test piece supporting base and the projection device are supported by a supporting part while being separate from and independent of each other.

With the foregoing configuration, the test piece supporting base and the projection device are supported by the supporting part while being separate from and independent of each other. For this reason, the foregoing configuration makes it less likely that an impact, which is generated when the projectile is projected by the projection device, may be transmitted to the test piece supported by the test piece supporting base, and thus makes it possible to prevent the impact from reducing the precision with which it is checked how the projectile collides with the test piece and how the test piece is damaged.

According to a seventh feature of the present invention, there is provided a collision test method of colliding a projectile projected from a projection device with a test piece supported by a test piece supporting base for checking a state of collision of the projectile with the test piece or how the test piece is damaged thereby, the collision test method comprising the steps of: pulling a projectile supporting part supporting the projectile while deforming an elastic body; arresting the projectile supporting part thus pulled; releasing the projectile supporting part from an arrested state, and thus accelerating the projectile supporting part by use of a restoring force of the elastic body; and colliding the projectile projected from the projectile supporting part with the test piece.

With the foregoing configuration, the projection device is constructed by connecting the projectile supporting part to the frame by use of the elastic body. The projectile supporting part supporting the projectile is pulled while deforming the elastic body, and the projectile supporting part thus pulled is arrested. The projectile supporting part is released from an arrested state, and thus the projectile supporting part is accelerated by use of the restoring force of the elastic body thereby to project the projectile. The projectile is collided with the test piece supported by the test piece supporting base. Thereby, the foregoing configuration makes it possible to check a state of collision of the projectile with the test piece or how the test piece is damaged thereby. Because the foregoing configuration causes the projectile to be projected by use of the restoring force of the elastic body thus deformed at an arbitrary timing, the foregoing configuration makes the collision test apparatus simple and compact in structure, low costs, and easy-to-handle in comparison with a configuration in which a projectile is projected by use of compressed air.

Note that: a floor 11 of the embodiments corresponds to the supporting part of the present invention; a spring supporting frame 22 of the embodiments corresponds to the frame of the present invention; coil springs 25 of the embodiments correspond to the elastic body of the present invention; a winch 34 of the embodiments corresponds to the pulling means of the present invention; and a pin 38 of the embodiments corresponds to the locking means of the present invention.

The above-described and other objects, characteristics and advantages of the present invention will be clear from the following detailed descriptions of preferred embodiments on the basis of the attached drawings.

BRIEF DESCRIPTION OF THE DRAWINGS

FIG. 1 is an overall perspective view of a collision test apparatus.

FIG. 2 is an enlarged view of an essential part of the collision test apparatus of FIG. 1.

FIG. 3 is a cross-sectional view taken along a line 3-3 in FIG. 2.

FIG. 4 is a cross-sectional view taken along a line 4-4 in FIG. 3.

FIG. 5 is a cross-sectional view taken along a line 5-5 in FIG. 3.

FIG. 6 is a view in a direction indicated by a line 6-6 in FIG. 3.

FIG. 7 is a view in a direction indicated by a line 7-7 in FIG. 4.

FIG. 8 corresponds to FIG. 2, and is a view for explaining how the collision test apparatus operates.

FIG. 9 corresponds to FIG. 4, and is a view for explaining how the collision test apparatus operates.

FIGS. 10 and 11 show a second embodiment of the present invention.

FIG. 10 is a view corresponding to FIG. 2.

FIG. 11 is a cross-sectional view taken along a line 11-11 in FIG. 10.

DESCRIPTION OF THE PREFERRED EMBODIMENTS

First of all, descriptions will be provided for a first embodiment of the present invention on the basis of FIGS. 1 to 9.

Figure 1:
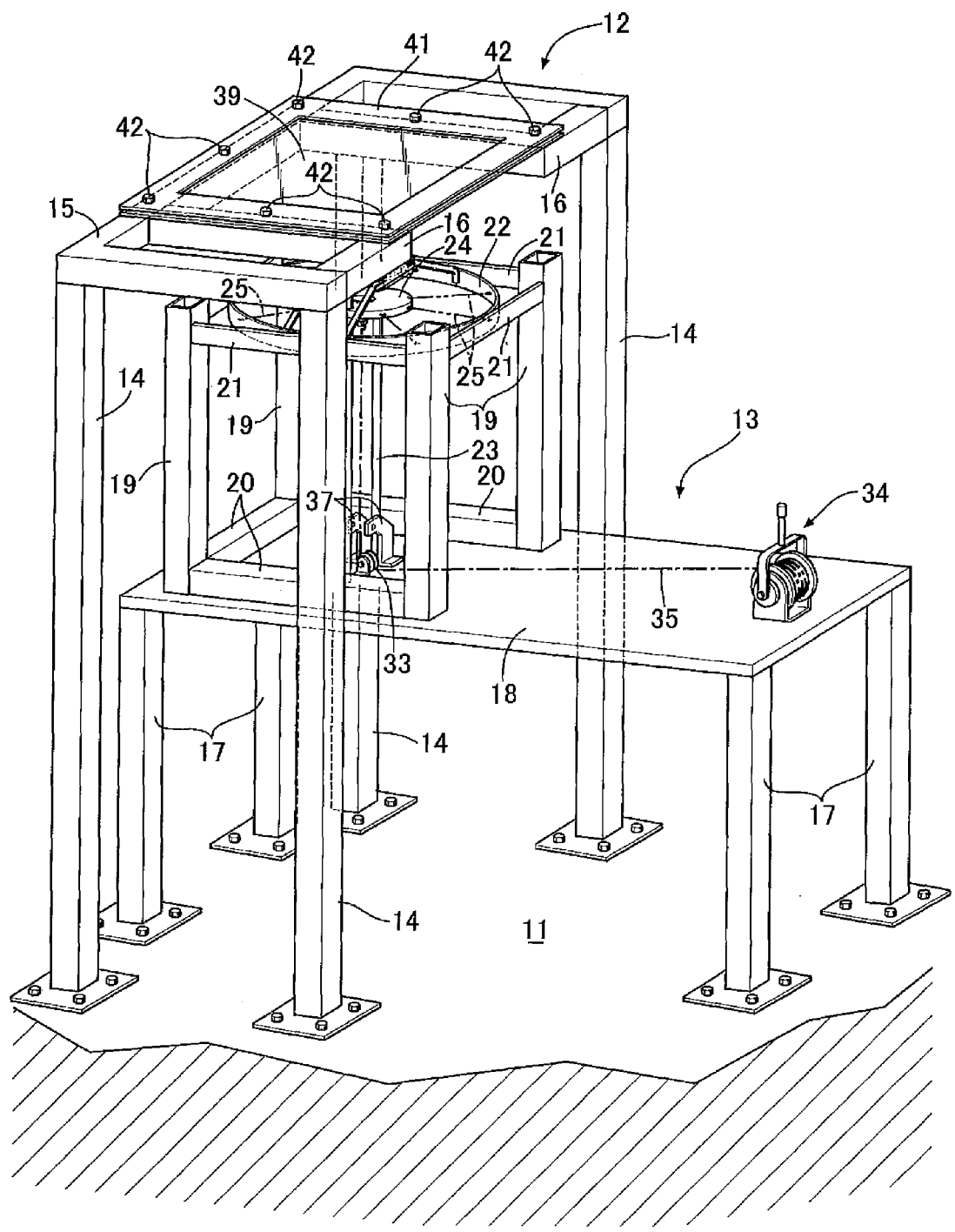
FIGS. 1 to 9 show a first embodiment of the present invention.
Figure 2:
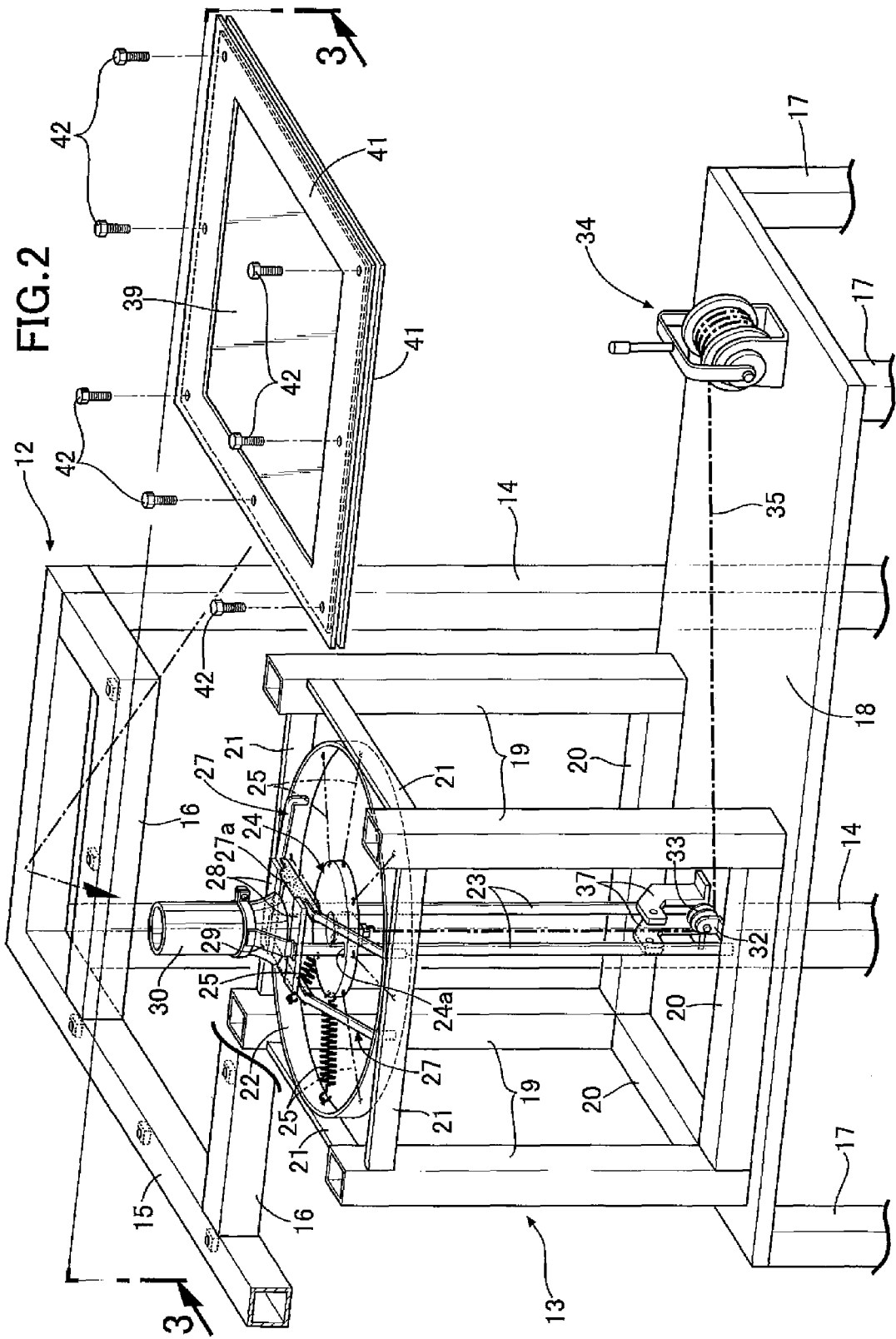
Figure 3:
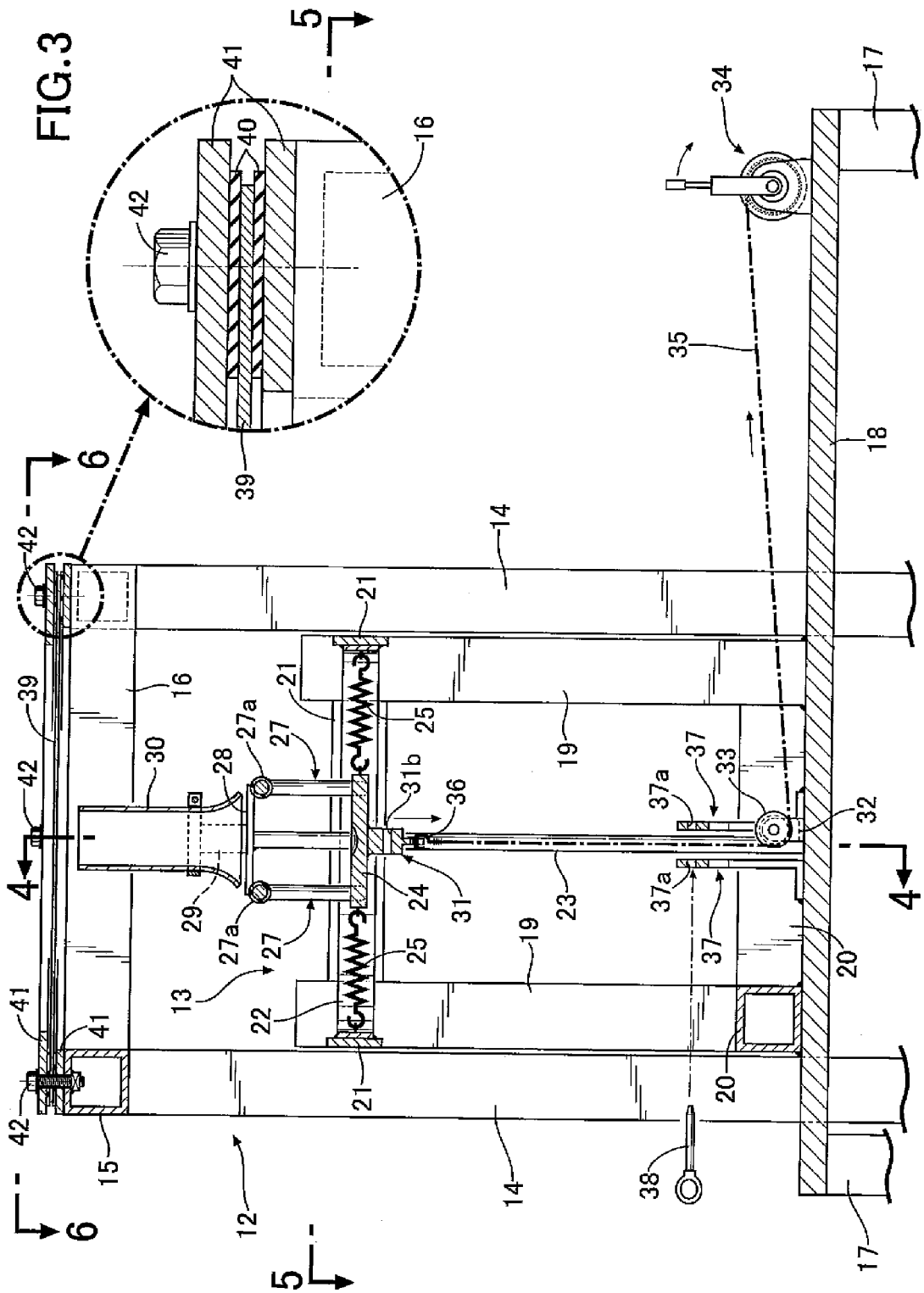
Figure 4:
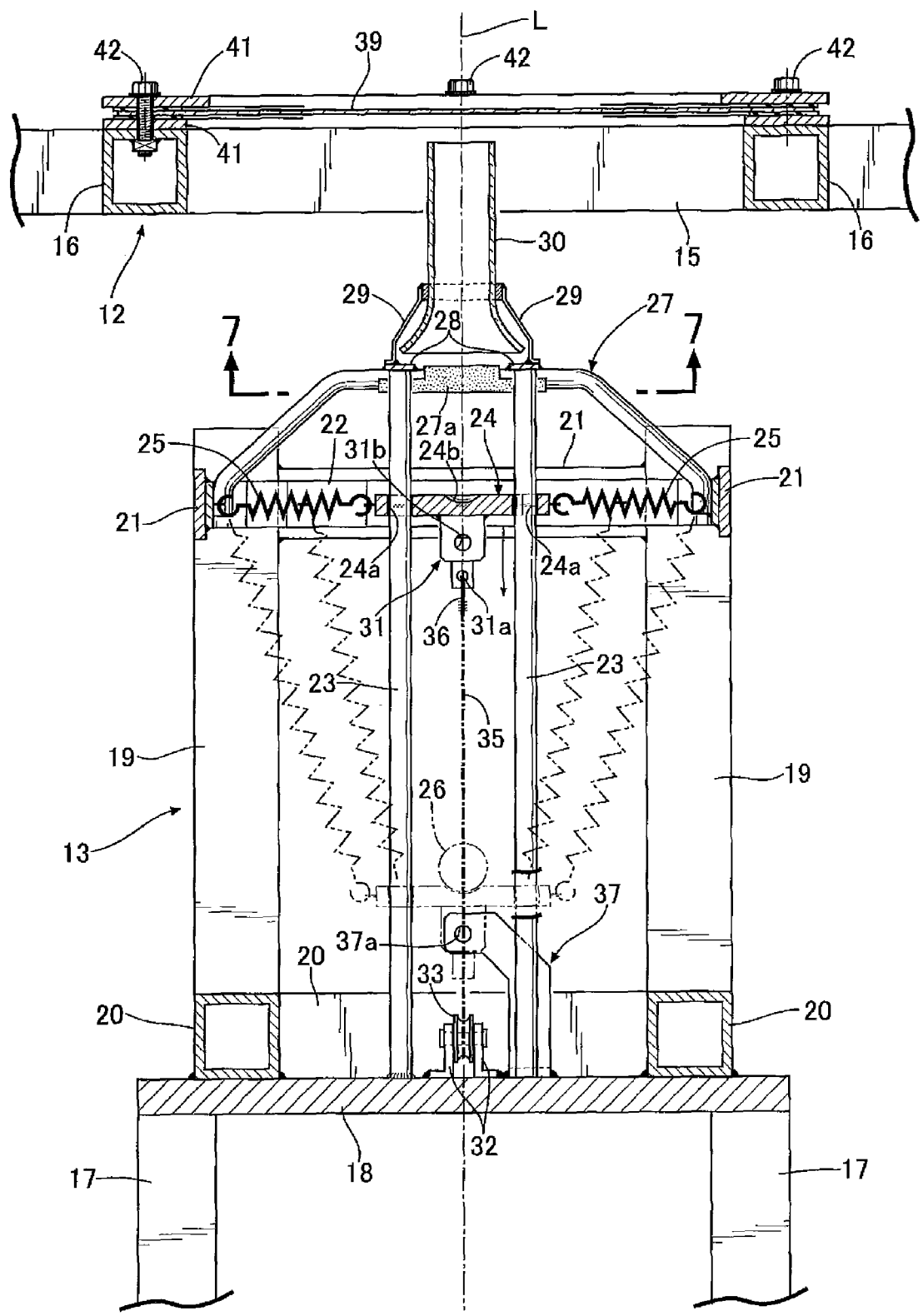
Figure 5:
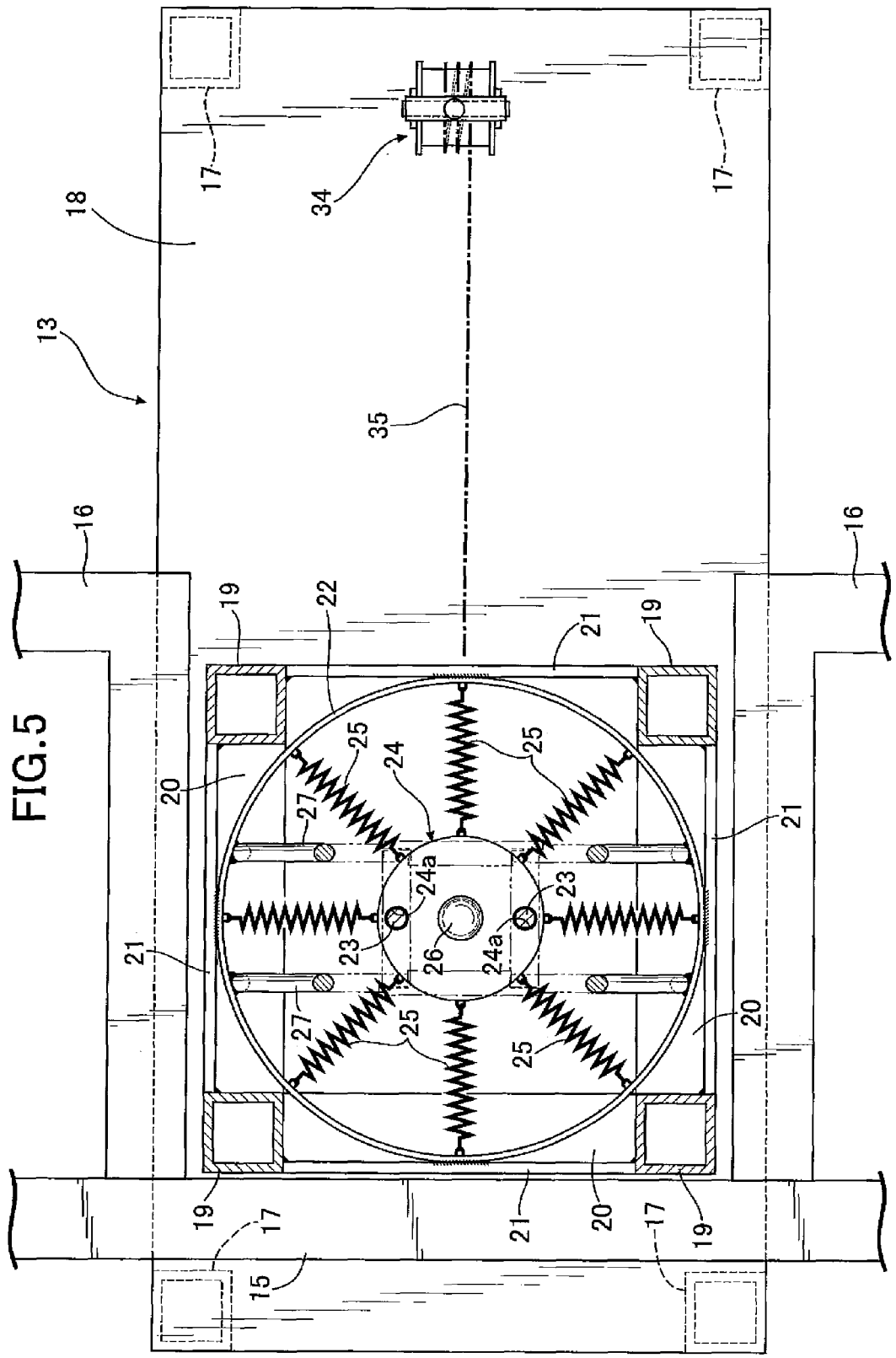
Figure 6:
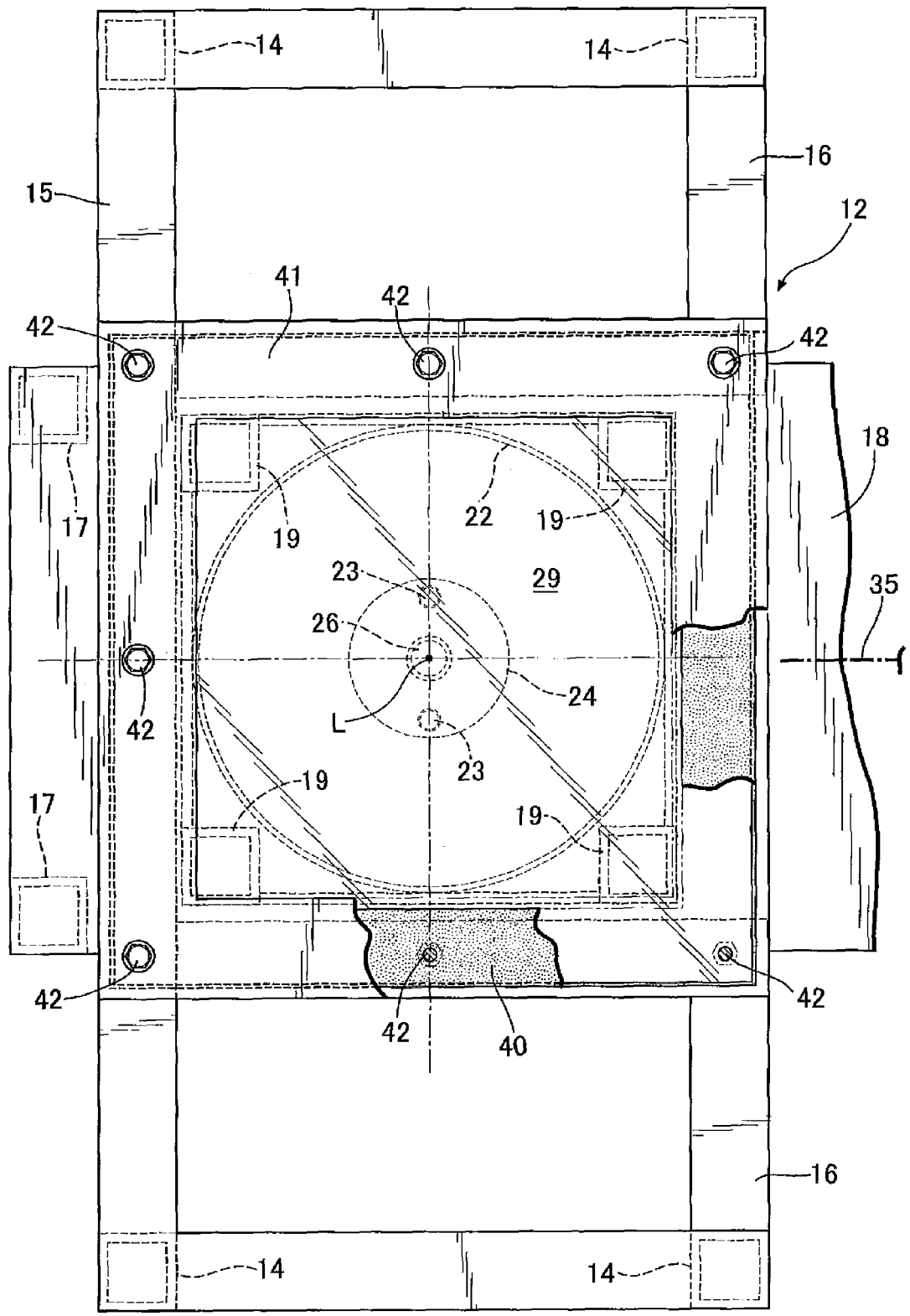
Figure 7:
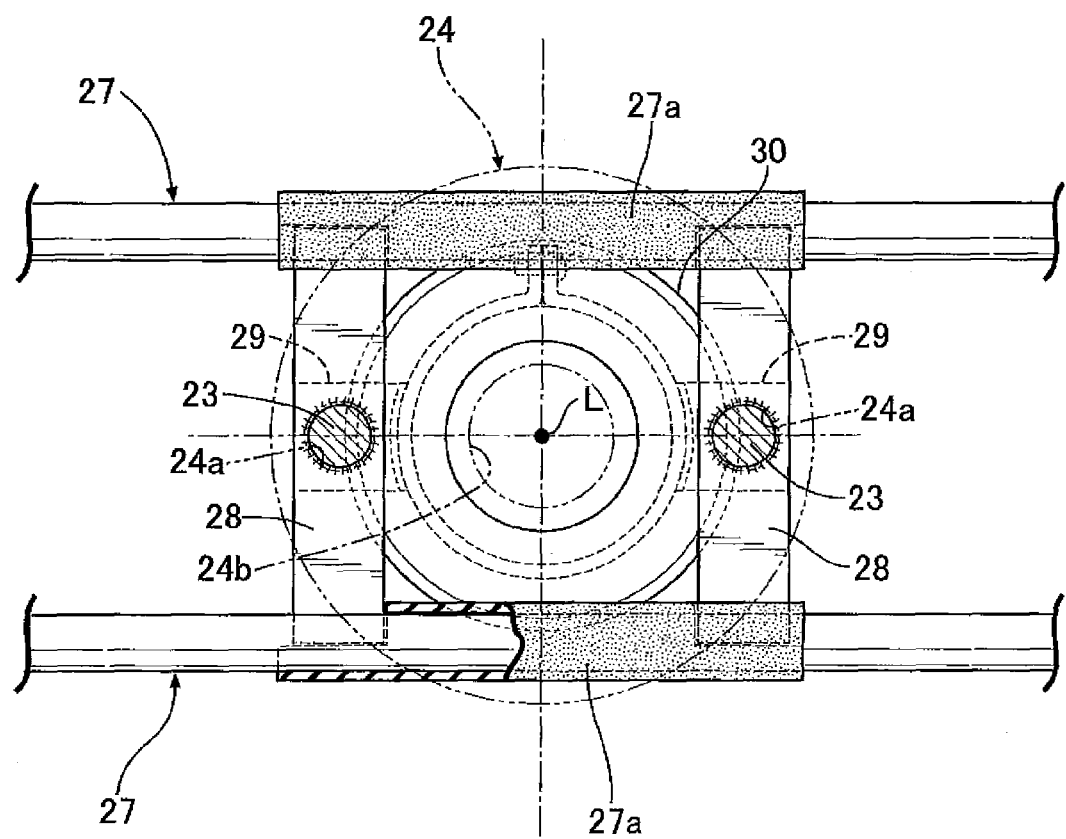
Figure 8:
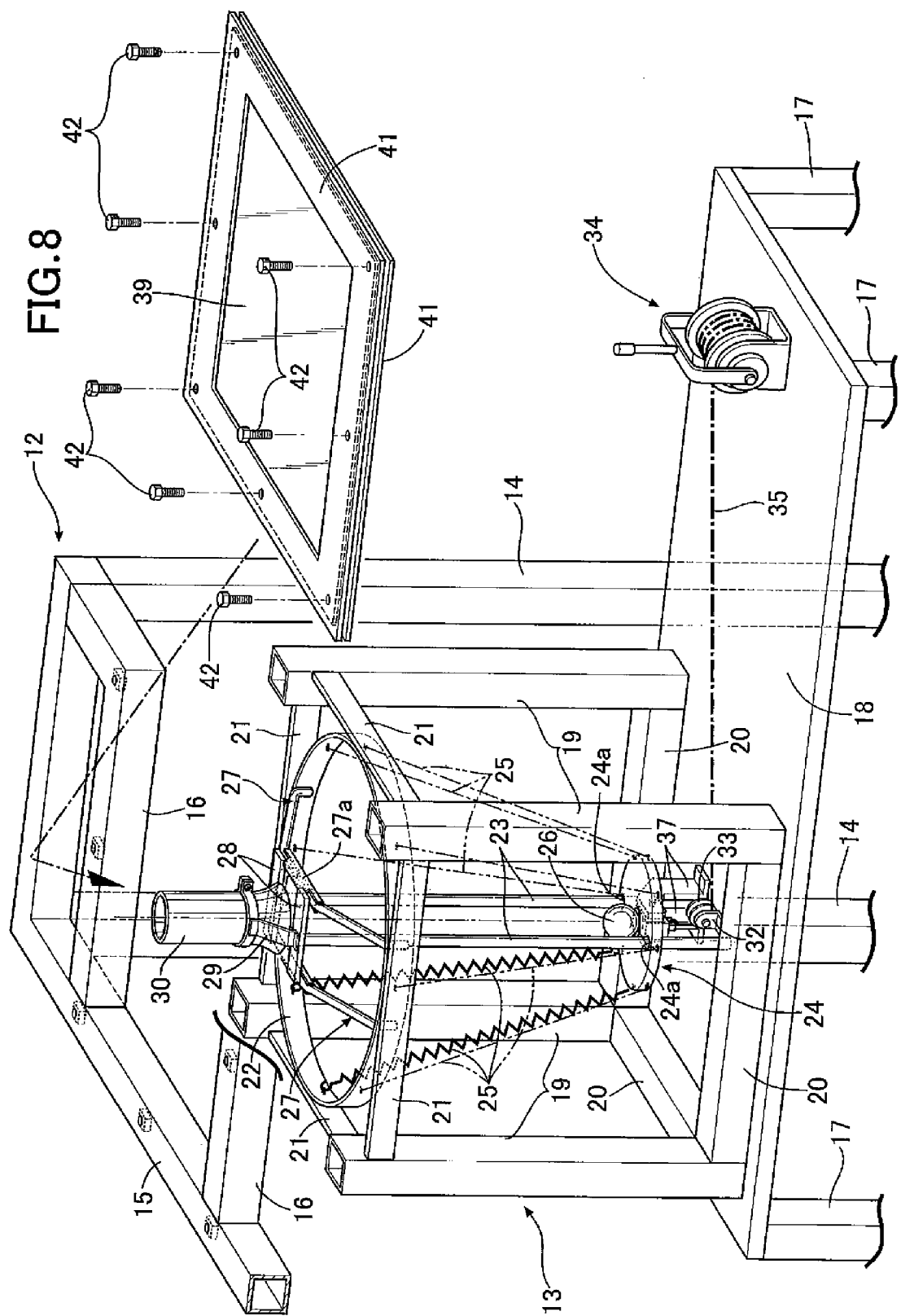
Figure 9:
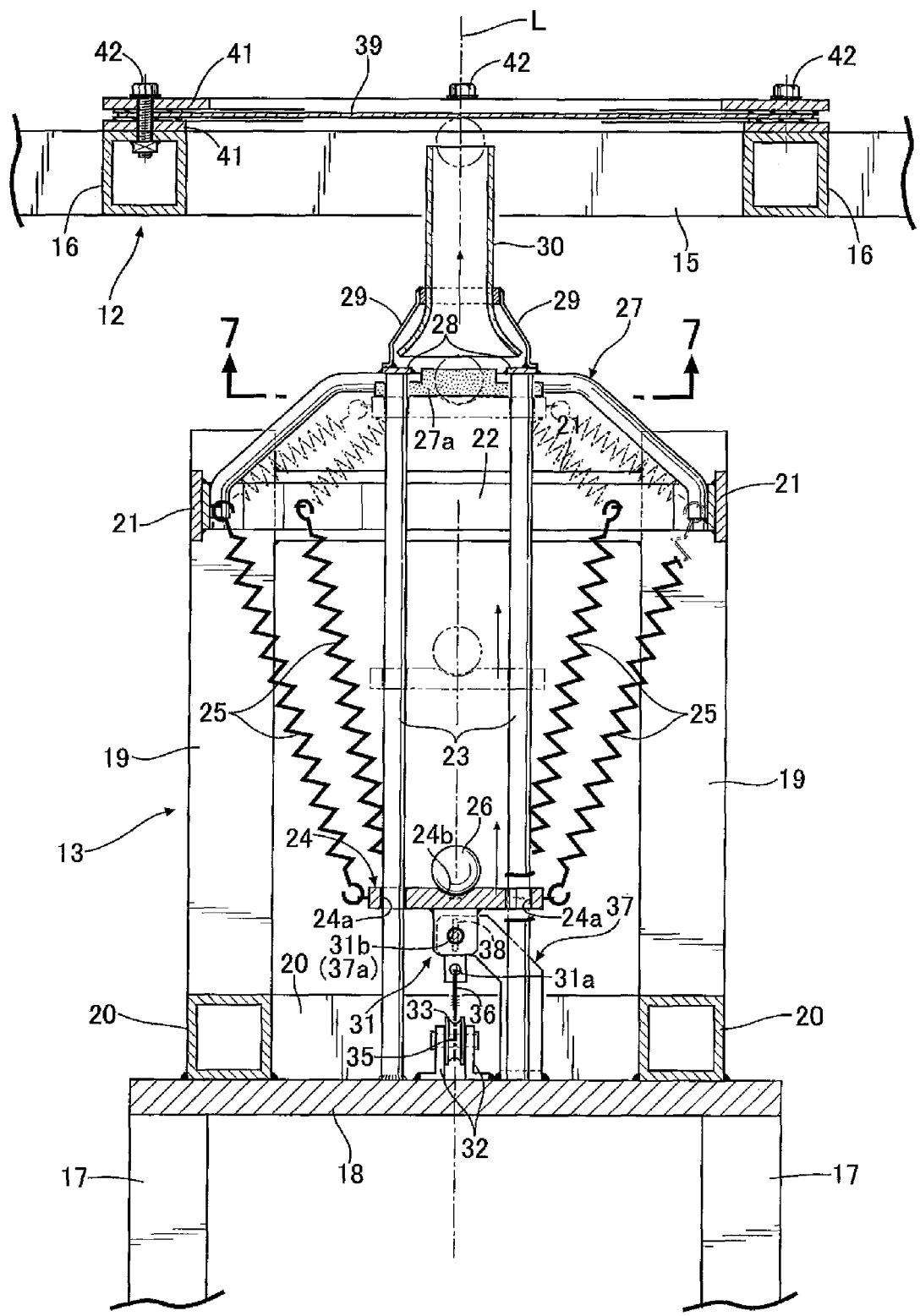

As shown in FIG. 1, a collision test apparatus supported by a floor 11 is configured of a test piece supporting base 12 and a projection device 13. The test piece supporting base 12 and the projection device 13 are supported by the floor 11 in a way that the test piece supporting base 12 and the projection device 13 are separate from and independent of each other. In other words, the test piece supporting base 12 and the projection device 13 are connected to each other through the floor 11 only, and are connected to each other through nothing but the floor 11.

The test piece supporting base 12 includes: four columns 14 installed upright on the floor 11; an angular U-shaped beam 15 with which the upper ends of the respective four columns 14 are connected to each other; and two L-shaped frame members 16, 16 connected to the beam 15 in the same plane.

The projection device 13 includes: four columns 17 installed upright on the floor 11; a rectangular base board 18 supported by the upper ends of the respective four columns 17 at its four corners; four columns 19 installed upright on the upper surface of an end portion side of the base board 18, that is to say, of the test piece supporting base 12 side; three reinforcement members 20 with which lower end portions of the respective four columns 19 are connected to each other; four beams 21 with which the upper ends of the respective four columns 19 are connected to each other; and a short cylindrical spring supporting frame 22 fixed to the inner surfaces of the respective four beams 21.

As shown in FIGS. 2 to 6, two guide rods 23, 23 are installed upright on the upper surface of the base board 18 in a vertical direction. The guide rods 23, 23 are respectively slidably fitted into two guide holes 24a, 24a that are formed in a disc-shaped projectile supporting part 24. Eight coil springs 25 are radially arranged at intervals of 45°. The inner circumferential surface of the spring supporting frame 22 is connected to one end of each coil spring 25, and the outer circumferential surface of the projectile supporting part 24 is connected to the other end of each coil sprint 25.

A partially-globular concave part 24b for supporting a projectile 26 is formed in the upper surface of the projectile supporting part 24. The project body 26 is formed as an ice ball with a diameter of 2.5 cm which imitates a piece of hail.

Two stoppers 27, 27 are bridged between two side ends of the spring supporting frame 22. Each of the two stoppers 27, 27 is curved upward like a mountain. Buffer members 27a, 27a are provided in the middle portions of the stoppers 27, respectively. The upper surface of the projectile supporting part 24 collides with the buffer members 27a, 27a. Top portions of the respective two stoppers 27, 27 are connected to each other with two connecting members 28, 28. The upper ends of the guide rods 23, 23 are respectively fixed to the connecting members 28, 28. A guide cylinder 30 with a circular cross-section is supported by the two connecting members 28, 28 in the vertical direction with a pair of stays 29, 29. The guide cylinder 30 is formed of a transparent synthetic resin, and has an opened lower portion which fans out like a funnel.

A protrusion part 31 is fixed to the lower surface of the projectile supporting part 24. A hook locking hole 31a and a pin locking hole 31b are formed in lower end portions of the protrusion part 31. A pulley 33 is rotatably supported by a bracket 32 provided on the upper surface, on an end side, of the base board 18, which corresponds to a portion downward of the projectile supporting part 24. A winch 34 is provided on the upper surface, on the other end side, of the base board 18. A wire 35 wound around a drum of the winch 34 is extended horizontally to the pulley 33, and thereafter extended upward via the pulley 33. A hook 36 provided in the upper end of the wire 35 is detachably locked in the hook locking hole 31a of the protrusion part 31.

Stays 37, 37 are provided in a vicinity of the pulley 33 on the upper surface of the base board 18. Pin locking holes 37a, 37a are formed in upper portions of the stays 37, 37, respectively. When the projectile supporting part 24 is lowered enough, the pin locking hole 31b of the protrusion part 31 and the pin locking holes 37a, 37a of the respective stays 37, 37 coincide with each other. By inserting a pin 38 into the coinciding pin locking holes 31b, 37a, 37a, the projectile supporting part 24 is locked to the base board 18.

A target collision position in a test piece 39, the center of the guide cylinder 30, the concave part 24b of the projectile supporting part 24, the hook locking hole 31a and the pin locking hole 31b of the protrusion part 31 provided to the projectile supporting part 24, as well as the intermediate position between the pin locking holes 37a, 37a of the respective paired stays 37, 37 are aligned on an axis line L which extends in the vertical direction.

The test piece 39 is obtained by cutting out an outer skin of an aircraft into a rectangular piece. The test piece 39 is sandwiched between two supporting frames 41, 41 with a buffering member 40 being interposed between each supporting frame 41 and its corresponding outer periphery of the test piece 39. The two supporting frames 41, 41 are detachably fixed to the upper surfaces respectively of the beam 15 and the frame members 16, 16 of the test piece supporting base 12 by use of multiple bolts 42.

Next, descriptions will be provided for how the first embodiment of the present invention with the foregoing configuration operates.

The supporting frames 41, 41 are fixed to the test piece supporting base 12 by use of the bolts 42 with the test piece 39 being attached to the supporting frames 41, 41. While the supporting frames 41, 41 are being fixed thereto, the hook 36 provided to the tip end of the wire 35 is locked in the hook locking hole 31a formed in the protrusion part 31 provided to the projectile supporting part 24. The wire 35 is wound up by manipulating the winch 34. Thereby, the projectile supporting part 24 is pulled downward along the guide rods 23, 23 while the eight coil springs 25 are being expanded. When the pin locking hole 31b formed in the protrusion part 31 provided to the projectile supporting part 24 comes to coincide with the pin locking holes 37a, 37a formed in the respective stays 37, 37 provided to the base board 18, the pin 38 is inserted into the three pin locking holes 31b, 37a, 37a. This insertion causes the projectile supporting part 24 to be arrested by the base board 18 (see FIGS. 8 and 9).

Subsequently, the hook 36 provided to the wire 35 is removed from the hook locking hole 31a of the protrusion part 31 provided to the projectile supporting part 24, and the projectile 26 is placed on the partially-globular concave part 24b in the projectile supporting part 24. Once the projectile 26 is thus ready to be projected, the pin 38 is pulled out of the pin locking holes 31b, 37a, 37a, and thereby the projectile supporting part 24 is released from an arrested state. As a result, the projectile supporting part 24 is accelerated upward along the two guide rods 23, 23 by contraction forces of the respective coil springs 25 which have been expanded. When the speed of the projectile supporting part 24 comes to its maximum, that is to say, when the coil springs 25 start to expand after completely contracting, the projectile 26 is lifted off from the projectile supporting part 24, and thus projected upward.

When the coil springs 25 start to expand after completely contracting, the projectile supporting part 24 which has been so far accelerated starts to decelerate. At this time, the projectile 26 is projected from the projectile supporting part 24. This projection scheme makes it possible to stabilize the movement trajectory of the projectile supporting part 24 and the projection direction of the projectile 26 in comparison with a projection scheme of projecting the projectile 26 by colliding the projectile supporting part 24 with the stoppers while the projectile supporting part 24 is still in the process of being accelerated.

The projectile 26 thus projected is guided by the guide cylinder 30 whose lower portion fanning-out like a funnel. Thereby, the projectile 26 continues moving upward along the vertical flight line. Thus, the projectile 26 collides with the undersurface of the test piece 39 in the vertical direction. After the projectile 26 is projected therefrom, the projectile supporting part 24 continues increasing its inertia. However, the projectile supporting part 24 stops after abutting on the buffer member 27a, 27a of the respective stoppers 27. This makes it possible to prevent the projectile supporting part 24 from overpassing its initial position to a large extent, and thus to prevent the projectile supporting part 24 from interfering with any other body. The projectile supporting part 24 abuts on the stoppers 27, 27, only after the projectile 26 is projected from the projectile supporting part 24. For this reason, an impact generated by the abutment is unlikely to deviate the projection direction of the projectile 26 from the expected direction.

For the collision test, it is judged whether or not the projectile 26 has collided with the test piece 39 in a normal condition. Specifically, the collision speed of the projectile 26 is detected by photographing the projectile 26 passing the inside of the transparent guide cylinder 30 with an ultra high speed camera. In the case of the present embodiment, when the collision speed of the projectile 26 is in a range of 82 km/h±2 km/h, it is judged that the projectile 26 has collided with the test piece 39 in the normal condition. In addition, the collision position of the projectile 26 is detected by adhering a pressure-sensitive sheet to the undersurface of the test piece 39. In the case of the present embodiment, when the deviation of the projectile 26 from the target collision position is within 3 mm, it is judged that the projectile 26 has collided with the test piece 39 in the normal condition.

TABLE 1

| SAMPLE NO. | COLLISION SPEED (km/h) |
|---|---|
| 1 | 79.8 |
| 2 | 81.1 |
| 3 | 80.0 |
| 4 | 82.9 |
| 5 | 81.3 |

Table 1 shows a result of detecting collision speeds. Out of the collision speeds of Samples 1 to 5, the collision Sample 1 fell outside the range of 82 km/h±2 km/h, and the collision speeds of Samples 2, 3, 4 and 5 fell inside the range of 82 km/h±2 km/h.

TABLE 2

| SAMPLE NO. | DEVIATION FROM TARGET COLLISION POSITION (mm) |
|---|---|
| 1 | 0.5 |
| 2 | 2.0 |
| 3 | 2.0 |
| 4 | 3.0 |
| 5 | 3.0 |

Table 2 shows a result of detecting collision positions. All of the deviations of the collision positions of Samples 1 to 5 from the target collision position were within 3 mm.

The displacement of the test piece 39 due to the collision is detected with a laser displacement gauge. The distortion of the test piece 39 due to the collision is detected with a distortion gauge. The impact load on the test piece 39 is detected with a load cell. How the test piece 39 has been damaged is evaluated visibly and by use of other means after the test piece 39 is detached from the test piece supporting base 12.

The test piece supporting base 12 for supporting the test piece 39 and the projection device 13 for projecting the projectile 26 are supported by the floor 11 in a way that the test piece supporting base 12 and the projection device 13 are separate from and independent of each other. For this reason, the impact caused by the projection of the projectile 26 by the projection device 13 is less likely to be transmitted to the test piece 39 supported by the test piece supporting base 12. In addition, the supporting scheme obviates the influence of the vibrations and impact caused by the projection on the test piece 39 itself and the measuring instruments. For these reason, it is possible to prevent the reduction of precision with which it is checked a state of collision of the projectile 26 with the test piece 39 or how the test piece 39 is damaged thereby.

As described above, the projectile 26 is projected by use of restoring forces of the respective coil springs 25 that are once deformed by expansion. This projection scheme not only makes it possible to easily obtain an arbitrary target collision speed by adjusting the coil springs 25 stronger or weaker, or by replacing the coil springs 25 with new ones, but also makes the collision test apparatus compact in size, easy-to-handle, simple in structure, and low cost in comparison with a projection scheme of projecting a projectile by use of compressed air or the like. Moreover, because the projectile supporting part 24 is locked by use of the pin 38 while being pulled with the wire 35 by the winch 34, and because the projectile supporting part 24 is released from the locking by pulling the pin 38 out, it is easy not only to pull the projectile supporting part 24, but also to project the projectile 26 at an arbitrary timing.

Additionally, because the guide holes 24a, 24a formed in the projectile supporting part 24 are guided by the respective guide rods 23, 23, it is possible to stabilize the movement trajectory of the projectile supporting part 24 when the projectile 26 is projected from the projectile supporting part 24, and to reduce the deviation of the projection direction of the projectile 26 to a minimum. Furthermore, because the projectile 26 projected from the projectile supporting part 24 is guided to the test piece 39 through the guide cylinder 30, it is possible to correct the projection direction of the projectile 26 by use of the guide cylinder 30, and thus to cause the projectile 26 to collide with the test piece 39 at the target collision position set up on the test piece 39, even if the projection direction of the projectile 26 deviates to some extent.

Figure 10:
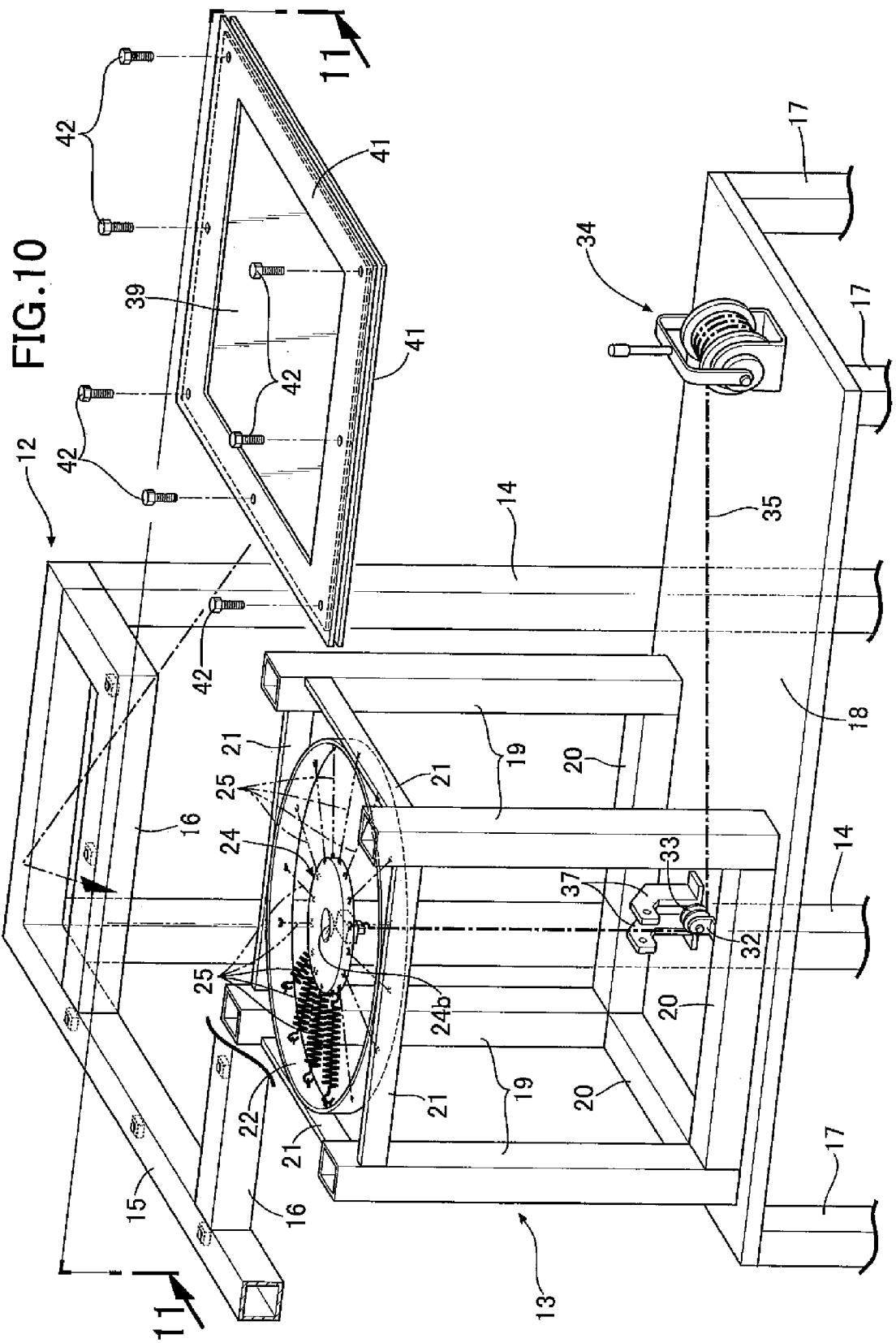

Next, descriptions will be provided for a second embodiment of the present invention on the basis of FIGS. 10 and 11.

The collision test apparatus according to the first embodiment (see FIGS. 2 and 3) includes: the two guide rods 23, 23 for guiding the movement of the projectile supporting part 24; and the guide cylinder 30 for guiding the projectile 26 projected toward the test piece 39. By contrast, a collision test apparatus according to a second embodiment includes neither the guide rods 23, 23 nor the guide cylinder 30.

The collision test apparatus according to the second embodiment is different from the collision test apparatus according to the first embodiment in that the collision test apparatus according to the first embodiment causes the projectile supporting part 24 to be driven by use of the eight coil springs 25, and in that the collision test apparatus according to the second embodiment causes the projectile supporting part 24 to be driven by use of 16 coils sprints 25, which are twice as many as the eight coil springs of the collision test apparatus according to the first embodiment. The increase of the number of coil springs 25 stabilizes the posture of the projectile supporting part 24 when the projectile 26 is projected from the projectile supporting part 24. For this reason, the collision test apparatus according to the second embodiment is capable of colliding the projectile 26 with the test piece 39 at its right position although neither the guide rods 23, 23 nor the guide cylinder 30 are included in the collision test apparatus.

In addition, the increase of the number of coil springs 25 to 16 makes the collision test apparatus according to the second embodiment capable of increasing the collision speed at which the projectile 26 collides with the test piece 39 in comparison with the collision test apparatus according to the first embodiment, even if the diameter of an ice ball as the projectile 26 is increased to 3.75 cm which is 1.5 times as large as 2.5 cm which is the diameter of an ice ball as the projectile 26 used in the collision test apparatus according to the first embodiment, or even if the diameter of an ice ball as the projectile 26 is increased to 5 cm which is twice as large as 2.5 cm.

The first embodiment causes the collision test apparatus to collide the projectile 26 with a diameter of 2.5 cm with the test piece 39 at a collision speed of 82 km/h±2 km/h. As learned from Table 3, the second embodiment makes the collision test apparatus capable of colliding the projectile 26 with a diameter of 3.75 cm with the test piece 39 at a collision speed of 100.43 km/h, and capable of colliding the projectile 26 with a diameter of 5 cm with the test piece 39 at a collision speed of 115.97 km/h.

TABLE 3

| SAMPLE NO. | COLLISION SPEED (km/h) | CONDITION OF TEST PIECE |
|---|---|---|
| 1 | 100.43 | GOOD |
| 2 | | SMALL CRACK (L 2.6 × d 3.9) |
| 3 | | GOOD |
| 4 | 115.97 | SMALL CRACK (L 5.5 × d 4.0) |
| 5 | | MEDIUM CRACK (L 7.3 × d 2.9) |
| 6 | | LARGE CRACK (L 27.1 × d 5.4) |

L: VERTICAL LENGTH OF CRACK (IN LONGITUDINAL DIRECTION)
d: HORIZONTAL LENGTH OF CRACK (IN DIRECTION PERPENDICULAR TO LONGITUDINAL DIRECTION)

Note that, in Table 3, letter "L" denotes the vertical length of a crack (in the longitudinal direction), and letter "d" denotes the horizontal width of the same crack (in a direction perpendicular to the longitudinal direction).

In the case of the projectile 26 with a diameter of 3.75 cm, a small crack was observed in the single test piece 39 out of Sample 1 to 3. In the case of the projectile 26 with a diameter of 5 cm, a small crack was observed in the single test piece 39 out of Samples 4 to 6; a medium crack was observed in another single test piece 39 out of Samples 4 to 6; and a large crack was observed in the other single test piece 39 out of Samples 4 to 6.

The second embodiment increases the number of coil springs 25. Thereby, the second embodiment is not only capable of simplifying the structure of the collision test apparatus by causing the collision test apparatus to include neither the guide rods 23, 23 nor the guide cylinder 30, but also makes the collision test apparatus capable of colliding the projectile 26 with a larger diameter with the test piece 39 at a higher collision speed.

The foregoing descriptions have been provided for the embodiments of the present invention. However, the design of the present invention can be modified variously without departing from the gist of the present invention.

For example, in the above embodiments, a piece of an outer skin of an aircraft is used as the test piece 39. The test piece 39 of the present invention is of an arbitrary type.

In addition, the elastic bodies for accelerating the projectile supporting part 24 are not limited to the coil springs 25. Elastic bodies of an arbitrary type may be used.

Moreover, the projectile 26 to be collided with the test piece 39 is not limited to the ice ball. A projectile of an arbitrary type may be used as the projectile 26.

What is claimed is:

1. A collision test apparatus which collides a projectile projected from a projection device with a test piece supported by a test piece supporting base for checking a state of collision of the projectile with the test piece or how the test piece is damaged thereby, wherein
    the projection device is configured by connecting a projectile supporting part to a frame by use of an elastic body which is connected to a plurality of peripherally distanced portions of said projectile supporting part,
    the projectile supporting part supporting the projectile is pulled while deforming the elastic body, and
    the projectile is projected upward along a vertical flight line and in a vertical direction from the projectile supporting part by use of a restoring force of the elastic body so as to collide with the test piece at an angle of 90°.

2. The collision test apparatus according to claim 1, wherein the projectile is projected from the projectile supporting part when the projectile supporting part starts to be decelerated after ceasing to be accelerated.

3. The collision test apparatus according to claim 1, comprising:
    pulling means for pulling the projectile supporting part by use of a wire; and
    locking means for locking the projectile supporting part to a pulling position,
    wherein the projectile is projected by releasing the projectile supporting part from being locked by the locking means.

4. The collision test apparatus according to claim 1, comprising a stopper for stopping the projectile supporting part by abutting on the projectile supporting part after the projectile is projected therefrom.

5. The collision test apparatus according to claim 1, comprising:
    a guide rod which is slidably fitted into a guide hole formed in the projectile supporting part, and
    a guide cylinder for guiding the projectile projected from the projectile supporting part to the test piece.

6. The collision test apparatus according to claim 1, wherein the test piece supporting base and the projection device are supported by a supporting part while being separate from and independent of each other.

7. The collision test apparatus according to claim 1, wherein as said elastic body, a plurality of elastic bodies are connected at their respective one end to said plurality of peripherally distanced portions of the projectile supporting part, said elastic bodies being connected at their respective other end to said frame.

8. The collision test apparatus according to claim 7, wherein each of said elastic bodies is a coil spring.

9. The collision test apparatus according to claim 1, wherein the projectile supporting part supporting the projectile is pulled in a first direction while deforming the elastic body, the test piece supporting base and the projection device are supported by a supporting part and are located on a top surface of the supporting part, and the first direction is perpendicular to the top surface of the supporting part.

10. The collision test apparatus according to claim 9, wherein the projectile supporting part is configured to be non-movable in a second direction parallel to the top surface of the supporting part.

11. The collision test apparatus according to claim 1, further comprising a pair of guide rods, each of the guide rods being slidably fitted into a corresponding guide hole formed in the projectile supporting part, a line connecting the center of the guide holes passing a vertical axis of the projectile supporting part.

12. The collision test apparatus according to claim 1, wherein the plurality of peripherally distanced portions of the projectile supporting part are more than two.

13. The collision test apparatus according to claim 1, wherein a number of elastic bodies are provided correspondingly to the plurality of peripherally distanced portions of the projectile supporting part and are connected to the frame in an annular arrangement at an equal distance to the projectile supporting part.

14. A collision test method of colliding a projectile projected from a projection device with a test piece supported by a test piece supporting base for checking a state of collision of the projectile with the test piece or how the test piece is damaged thereby, the collision test method comprising the steps of:
pulling a projectile supporting part supporting the projectile while deforming an elastic body which is connected to a plurality of peripherally distanced portions of said projectile supporting part;
arresting the projectile supporting part thus pulled;
releasing the projectile supporting part from an arrested state, and thus accelerating the projectile supporting part by use of a restoring force of the elastic body;
projecting the projectile upward along a vertical flight line and in a vertical direction from the projectile supporting part and colliding the projectile projected with the test piece at an angle of 90°.

15. The collision test method according to claim 14, wherein the test piece supporting base and the projection device are supported by a supporting part and located on a top surface of the supporting part, and the pulling step includes pulling the projectile supporting part supporting the projectile in a first direction perpendicular to the top surface of the supporting part while deforming an elastic body.

16. The collision test method according to claim 15, wherein the projectile supporting part is non-movable in a second direction parallel to the top surface of the supporting part.

* * * * *